United States Patent

Bolz et al.

[11] Patent Number: 5,776,926
[45] Date of Patent: Jul. 7, 1998

[54] CEFIXIME COMPOSITION

[75] Inventors: Joachim Bolz; Gertraud Wagner, both of Darmstadt; Eckhard Oelrich, Rossdorf; Dirk Radtke, Darmstadt, all of Germany

[73] Assignee: Merck Patent GmbH, Germany

[21] Appl. No.: 806,757

[22] Filed: Mar. 3, 1997

Related U.S. Application Data

[63] Continuation of Ser. No. 453,812, May 30, 1995, abandoned.

[30] Foreign Application Priority Data

May 31, 1994 [DE] Germany .......... 44 18 957.5

[51] Int. Cl.⁶ .................................................. A61K 31/545
[52] U.S. Cl. .............................................................. 514/200
[58] Field of Search ................................................ 514/200

[56] References Cited

U.S. PATENT DOCUMENTS 4,079,138  3/1978  Lin et al. .................. 424/246
5,100,887  3/1992  Adam et al. ............... 514/195
5,409,917  4/1995  Robinson et al. .......... 514/200

OTHER PUBLICATIONS

Faulkner et al., "Bioequivalency of Oral Suspension Formulations of . . . ", *Biopharmaceutics & Drug Disposition*, 10(2):205–211, 1989.

*Primary Examiner*—José G. Dees
*Assistant Examiner*—Michael A. Williamson
*Attorney, Agent, or Firm*—Millen, White, Zelano & Branigan, P.C.

[57] ABSTRACT

The invention relates to compositions in the form of cefixime-containing non-aqueous suspensions which have syrup-like characteristics, characterized in that they are free of thickening ancillary substances and contain a microfine powder of bulking agent with a particle size distribution with at least 80% by weight having a maximum diameter of 32 μm and a maximum of 5% by weight having a diameter larger than 50 μm, are very easily redispersible and are chemically stable.

11 Claims, No Drawings

CEFIXIME COMPOSITION

This application is a continuation of application Ser. No. 08/453,812, filed May 30, 1995 now abandoned.

The invention relates to pharmaceutical compositions in the form of suspensions which have syrup like characteristics and contain cefixime.

Cefixime is a cephalosporin antibiotic which can be administered orally and resembles, in respect of its structure, the spectrum of organisms and the beta-lactamase stability, the 3rd generation cephalosporins of the cefotaxime type which can be administered parenterally.

Like all representatives of this class of substances, it has a bactericidal action. The mechanism of action of cefixime is based on inhibition of bacterial cell wall synthesis. The acute toxicity of cefixime is negligibly low.

The active substance is therefore suitable for the treatment of acute and chronic infections of varying severity caused by cefixime-sensitive pathogens and amenable to oral therapy.

Cefixime has bactericidal effects and is effective, for example, for the following pathogens: *Streptococcus pneumoniae, Streptococcus pyogenes, Streptococcus agalactiae; Hamophilus influenzae, Neisseria gonorrhoeae, Escherichia coli, Proteus mirabilis, Proteus vulgaris, Klebsiella pneumoniae, Klebsiella oxytoca,* Enterobacter sp., *Pasteurella multocida,* Providencia sp., Salmonella sp., Shigella sp., *Citrobacter amalonaticus, Citrobacter diversus, Serratia marcescens.*

Cefixime-containing compositions have hitherto normally been used only in the form of solid dosage forms such as tablets, capsules, granules or powders. However, liquid compositions, for example in the form of suspensions, would be advantageous for the specific mode of action of cefixime, in particular with a view to a rapid buildup of serum levels. It is indeed possible for the commercially available solid dosage forms to be suspended before use, for example in water, and to be taken in this form. However, these are stable for only a short time (max. 2 weeks). Attempts to produce cefixime-containing finished drug products in the form of suspensions have failed to date because suspensions with long-term stability were unobtainable with conventional ancillary substances, and the active substance is sensitive to hydrolysis in aqueous solutions. In addition, in suspensions of this type the solid sedimented after a short time and was so agglomerated that in some cases resuspension was no longer possible. Furthermore, these suspensions not only lacked physical stability but also showed no chemical stability so that storage was impossible, even short-term storage.

U.S. Pat. No. 4,079,138 describes a permanent suspension with a non-aqueous basis- as vehicle for active substances which are sensitive to hydrolysis, with all the examples being directed at amoxicillin and ampicillin as antibiotic active substances. Furthermore, these compositions always contain, besides other ancillary substances, a silicate-based thickener.

However, addition of thickening silicates inevitably leads to a great increase in the rate of deposition and promotes cementation of the sediment in deposited suspensions so that satisfactory resuspension is no longer possible.

In addition, this document says nothing about the particle size distribution of the active substance and bulking agent, which means that uniformity of active substance distribution is not ensured.

SUMMARY OF THE INVENTION

An object of the invention is a process for the stabilization of pharmaceutical compositions in the form of cefixime containing suspensions and a corresponding stable composition as finished drug product.

Suitable choice of the additives for formulation of these pharmaceutical suspensions with a nonaqueous basis prevents sedimentation of the suspended particles or at least keeps it as small as possible. The intention of this is to ensure that the composition remains homogeneous and correspondingly usable even after lengthy storage. If sedimentation does take place over the course of time, satisfactory resuspension of the sediment should be ensured. Furthermore, suspensions for oral use ought to supply a taste sensation which is as pleasant as possible or at least neutral. In particular, the solid content must be incorporated in such a way that the latter or the solid particles are not perceived as unpleasant on intake, that is to say a high viscosity must be ensured. In the case of aqueous suspensions it is possible for the said properties normally to be achieved by adding viscosity-increasing liquids such as glycerol, propanediol, sorbitol solution and/or liquid polyethylene glycols. In the case of non-aqueous suspensions the viscosity may be increased by adding suspending agents and thickeners. Agents of this type which increase the viscosity are normally high molecular weight cellulose derivatives or polysaccharide gums, such as, for example, carboxymethylcelluloses, methylcelluloses, or else silicates such as, for example, Carbosils or Syloide. These additives have, however, the disadvantages described above so that addition thereof does not provide a satisfactory achievement of the object, as has been verified in a large number of experiments in which the suspending agents and thickeners which are essentially customary in the technology of pharmaceutical suspensions were tested.

To achieve the object of developing a stable, slowly sedimenting, non-cementing cefixime suspension with, at the same time, pleasant administration properties, it is necessary to dispense with thickener and ensure a particular particle size distribution of the bulking material. Homogeneity of dispersion of the active substance, and thus a correct single dose—even when taken by spoon—is ensured after shaking.

It has now been found that, surprisingly, stable compositions in the form of cefixime-containing suspensions can be obtained when the active substance is employed in micronized form, and a microfine powder of bulking material with a particle size distribution of about 80% by weight or greater, having a particle size of about 32 μm or less and a max. of about 2% by weight of a particle size of about 50 μm or larger, is used in these compositions and, at the same time, addition of thickening ancillary substances is dispensed with.

The invention accordingly relates to pharmaceutical compositions in the form of non-aqueous suspensions which have syrup-like characteristics, characterized in that they are free of thickening ancillary substances and contain a microfine powder of bulking agent with a particle size distribution with at least about 80% by weight having a maximum diameter of about 32 μm and a maximum of about 5% by weight having a diameter larger than 50 μm. Suspensions of this type are redispersible and chemically stable. An "easily redispersible and chemically stable" composition also comprises a bulking agent in an amount and particle size effective in rendering the composition substantially equivalent in dispersibility and chemical stability to a composition containing a bulking agent having a particle distribution of about 80% by weight or greater of a particle size of about 32 μm or less and a maximum of about 2% or 5% by weight of a particle size of about 50 μm or larger.

The invention furthermore relates to a composition of this type in which the suspension contains about 0.1–50% by weight of the-active substance in micronized form, and the latter is suspended in, triglycerides of medium chain-length fatty acids, i.e., a non-aqueous suspending media.

The invention furthermore relates to a composition which additionally contains a wetting agent in a concentration about 0.01%–1% by weight.

The compositions contain the active substance in micronized form in concentrations about 0.1–5% by weight, preferably 0.5–3, particularly preferably 1–2.5, % by weight. A particularly preferred active substance is cefixime. The compositions according to the invention may additionally contain other active substances stable in the non-aqueous medium. However, substances which are particularly suitable are those which belong to the cephalosporin class, such as, for example, cefalexin, cephradine or cefotaxime.

Suitable non-aqueous suspending media are oily, viscous liquids of natural or synthetic origin, such as, for example, arachis or sesame oil, fatty acid esters of polyethylene glycol or else mono-, di- or triglycerides of medium- to long-chain saturated or unsaturated fatty acids. Triglyceride esters are particularly preferred. Triglycerides of medium chain-length fatty acids with 12–20 C atoms are particularly preferred. The concentrations of the oils can be about 40–80% by weight, but particularly 50–75, preferably 60–70, % by weight. It is also possible to use mixtures of the natural and/or synthetic oily liquids.

Suitable bulking agents are sugars or sugar substitutes in the form of a microfine powder with a substantially fixed particle size distribution in respect of the active substance so that homogeneity of active substance distribution is ensured. The microfine powder of bulking agent must be constituted such that at least about 95% by weight of the particles do not exceed an average particle size of 50 µm and at least 80% by weight have a particle size smaller than 32 µm. In this way, it is possible to achieve a sufficient viscosity so that addition of thickening ancillary substances can be dispensed with and, at the same time, satisfactory physical and chemical stability is present. "Sufficient viscosity" means, e.g., that the solid particles which are evenly distributed in the liquid show a very slow sedimentation so that there is no gradient concentration detectable over several days or even weeks. A composition according to the present invention can be free of a thickening ancillary substance, e.g., a silicate-based thickener. A composition according to the present invention can include an amount of a thickening ancillary substance which does not contribute substantially to the viscosity of the composition, e.g., where "substantially" can be, e.g., less than 5%, 2%, 1%, 0.75%, 0.50%, preferably less than 0.1 weight %.

A particularly advantageous particle size distribution of the bulking agent is 50–90% by weight having a particle size 30 µm or smaller and 10–50% by weight have a particle size 30–50 µm, there having been no adverse effect on the stability and the properties of the suspension with a content not exceeding 2% by weight with a particle size 50–100 µm. Bulking materials in which 80% by weight have a particle size smaller than 32 µm and up to a maximum of 5% by weight have a particle size larger than 50 µm, while the other particles have a particle size 32–50 µm, are very particularly preferred.

A preferred bulking agent is sucrose or the sugar substitute isomaltol (Palatinit®). However, further suitable examples of bulking agents are also lactose, glucose, mannitol, xylitol or lactitol or mixtures thereof as long as the above mentioned particle size distribution is taken into account.

The content of bulking agents is about 10–40% by weight. A concentration of 25–35% by weight is preferred.

Micronized substances are for example prepared by lyophilization (dry freezing) or drying by atomization. Microfine powders are for example prepared by pulverizing in special mills, as known in the art. Microfine particles have a very small particle size, often smaller than micronized substances.

Further possible examples of additives and ancillary substances are wetting agents, which should, however, be present only in concentrations about 0.01–1% by weight, preferably 0.02–0.1% by weight. Suitable wetting agents are the surfactants known per se, for example those substances belonging to the classes of alkylbenzenesulphonates, alkanesulphonates, fatty alcohol sulphates, fatty alcohol ether sulphates, fatty alcohol ethoxylates, alkylphenol ethoxylates or alkylphosphonates. Polysorbates are particularly suitable, especially polysorbate 80.

Other possible additives are so-called anti-caking agents such as, for example, magnesium stearate, and flavorings to improve the taste of the suspensions. These additives are used in concentrations about 1% by weight or less, preferably 0.25% or less by weight. Addition of preservatives is unnecessary and has no effect on the stability and storability of the suspensions according to the invention.

The suspensions according to the invention are prepared in a manner known per se by mixing the components and homogenizing. When wetting agents such as polysorbate are used, these are initially dissolved or suspended in the hydrophobic solvent before the other components are added with continuous stirring. These can then be used to fill packaging means customary for pharmaceutical suspensions, such as, for example, bottles, drinkable ampoules or portion packs for oral administration. The active substance remains dispersed throughout a lengthy storage period (e.g., at least 5 years) without irreversible sedimentation, without agglomeration or deposition on the vessel walls. It can be suspended very easily after this storage period by shaking.

The range of medical uses of the suspensions according to the invention is completely analogous to that of the known dosage forms containing cefixime and/or other cephalosporins. They are suitable for the treatment of acute and chronic infections of varying severity caused by cefixime-sensitive pathogens and amenable to oral therapy; for example for the treatment of:

infections of the upper and lower respiratory tract
infections of the ear, nose and throat region such as, for example, inflammation of- the middle ear (otitis media), sinus inflammations (sinusitis), infections of the tonsils and of the pharyngeal space (tonsillitis, pharyngitis, laryngitis)
infections of the kidneys and the urinary tract
infections of the biliary tract or
acute, gonorrhoeal urethritis.

The following dosage is recommended:

Children 12 years of age or younger receive, e.g., about 8 mg of cefixime/kg of body weight each day. The recommended dose can be administered alternatively all at once or divided into 2 single doses (e.g., about 4 mg of cefixime/kg of body weight in the morning and evening). An increase in the daily dose to 2×6 mg of cefixime/kg of body weight is possible depending on the severity and the location of the infection.

Adults and children above 12 years of age may receive 400 mg of cefixime each day. The recommended daily dose may be administered alternatively all at once or divided into 2 single doses (in the morning and 35 evening).

The dose should be reduced for patients with distinctly impaired renal function. The following examples describe the invention in detail without, however, restricting it.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding German application P 44 18 957.5, are hereby incorporated by reference.

|  | mg/5 ml | % by weight |
|---|---|---|
| Example 1 | | |
| Cefixime (micronized) | 100.0 | 1.82 |
| Polysorbate | 2.5 | 0.05 |
| Fruit flavor (raspberry) | 4.0 | 0.07 |
| Magnesium stearate | 8.5 | 0.16 |
| Sucrose (microfine powder) | 1700.0 | 31.03 |
| Medium chain-length triglycerides | 3663.0 | 66.87 |
|  | 5478.0 | 100.00 |
| Example 2 | | |
| Cefixime (micronized) | 136.6 | 2.50 |
| Polysorbate 80 | 2.5 | 0.05 |
| Fruit flavor (strawberry) | 3.0 | 0.05 |
| Sucrose (microfine powder) | 1650.0 | 30.19 |
| Medium chain-length triglycerides | 3673.0 | 67.21 |
|  | 5465.1 | 100.00 |
| Example 3 | | |
| Cefixime (micronized) | 100.0 | 1.82 |
| Polysorbate 80 | 2.5 | 0.05 |
| Fruit flavor (banana) | 4.0 | 0.07 |
| Magnesium stearate | 8.5 | 0.16 |
| Isomaltol (microfine powder) | 1700.0 | 31.03 |
| Medium chain-length triglycerides | 3663.0 | 66.87 |
|  | 5478.0 | 100.00 |
| Example 4 | | |
| Cefixime (micronized) | 136.6 | 2.50 |
| Polysorbate 80 | 2.5 | 0.05 |
| Fruit flavor (raspberry) | 3.0 | 0.05 |
| Mannitol (microfine powder) | 1650.0 | 30.19 |
| Medium chain-length triglycerides | 3673.0 | 67.21 |
|  | 5465.1 | 100.00 |

The following descriptions show the stability of the suspensions according to the invention.

Resuspendability

To determine the resuspendability, bottles after preparation and after storage (for up to 5 years) were shaken and 10 portions each of 1 ml were analyzed (mg of cefixime/5 ml of suspension):

|  | after preparation | after 60 months |
|---|---|---|
| 1st removal | 97.1 | 95.2 |
| 2nd removal | 97.2 | 95.6 |
| 3rd removal | 97.3 | 95.4 |
| 4th removal | 97.4 | 95.5 |
| 5th removal | 97.0 | 95.1 |
| 6th removal | 97.0 | 95.3 |
| 7th removal | 97.3 | 95.5 |
| 8th removal | 96.9 | 95.3 |
| 9th removal | 97.7 | 94.9 |
| 10th removal | 97.1 | 95.1 |

Storability after opening

To check the storability after opening, 5 or 10 ml of suspension were removed each day from bottles (containing 100 ml) for a period of 14 days. The cefixime content of the amounts removed on days 1, 5, 10 and 14 was determined:

Day 1 104.4 mg/5 ml
Day 5 105.2 mg/5 ml
Day 10 105.1 mg/5 ml
Day 14 105.2 mg/5 ml

Chemical stability

Storage at 23° C.; 50% relative humidity

| Storage times | Appearance | Cefixime | Deg. 2 | Deg. 3 |
|---|---|---|---|---|
| Start | white or pale yellowish suspension | 102.6 mg | 1.1 mg | 0.1 mg |
| 6 months | virtually unchanged | 99.0 mg | 1.4 mg | 0.2 mg |
| 12 months | virtually unchanged | 99.4 mg | 1.9 mg | 0.3 mg |
| 18 months | virtually unchanged | 99.8 mg | 1.8 mg | 0.3 mg |
| 24 months | virtually unchanged | 96.5 mg | 1.8 mg | 0.5 mg |
| 60 months | virtually unchanged | 95.3 mg | 2.4 mg | 1.0 mg |

(Deg. = degradation)

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A pharmaceutical composition, comprising (1) 0.1–5% by weight of micronized cefixime; (2) a non-aqueous suspending media; and (3) a microfine powder of a bulking agent containing a particle size distribution of 80% by weight or greater of a particle size diameter of 32 μm or less; and 5% by weight or less of a particle size diameter of 50 μm or greater, wherein the composition comprises less than 0.1 weight % of a thickening ancillary substance.

2. A pharmaceutical composition according to claim 1, comprising 0.5–3% by weight of micronized cefixime.

3. A pharmaceutical composition according to claim 1, wherein the non-aqueous suspending media is a triglyceride of medium chain-length fatty acid.

4. A pharmaceutical composition according to claim 3, wherein the medium chain-length fatty acid contains 12–20 carbon atoms.

5. A pharmaceutical composition according to claim 1, wherein the bulking agent is sucrose, isomaltol, or mannitol.

6. A pharmaceutical composition according to claim 1, further comprising a 0.01–1% by weight of a wetting agent.

7. A pharmaceutical composition according to claim 6, wherein the wetting agent is polysorbate 80.

8. A pharmaceutical composition according to claim 1, wherein the ancillary substance is a silicate-based thickener.

9. A method of treating a bacterial infection, comprising administering an effective amount of a composition according to claim 1.

10. A method according to claim 9, wherein 8 mg of cefixime/kg of body weight is administered per day.

11. A method according to claim 9, wherein 400 mg of cefixime is administered each day.

* * * * *